(12) United States Patent
Mueller

(10) Patent No.: US 12,708,381 B2
(45) Date of Patent: Aug. 18, 2026

(54) ORTHOPEDIC SHOULDER GUIDE

(71) Applicant: Zimmer, Inc., Warsaw, IN (US)

(72) Inventor: Michael Mueller, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 163 days.

(21) Appl. No.: 18/443,602

(22) Filed: Feb. 16, 2024

(65) Prior Publication Data

US 2024/0277351 A1 Aug. 22, 2024

Related U.S. Application Data

(60) Provisional application No. 63/447,372, filed on Feb. 22, 2023.

(51) Int. Cl.
*A61F 2/46* (2006.01)
*A61B 17/17* (2006.01)

(52) U.S. Cl.
CPC ........ *A61B 17/1778* (2016.11); *A61F 2/4612* (2013.01)

(58) Field of Classification Search
CPC .................. A61F 2/4003; A61F 2/4612; A61F 2002/3809; A61F 2002/3822; A61B 17/1684; A61B 17/1778
See application file for complete search history.

(56) References Cited

U.S. PATENT DOCUMENTS 6,277,123 B1 * 8/2001 Maroney ............... A61F 2/4657 606/99
7,341,593 B2 * 3/2008 Auxepaules .......... A61F 2/4609 606/91
7,608,109 B2 * 10/2009 Dalla Pria ............. A61F 2/4081 623/19.13
9,320,619 B2 * 4/2016 Anthony ................ A61B 17/16
9,757,238 B2 * 9/2017 Metzger ................ A61F 2/5046
10,085,856 B2 10/2018 Anthony et al.
10,736,697 B2 * 8/2020 Chaoui ................. A61F 2/4014
10,842,650 B2 * 11/2020 Poncet .................. A61F 2/4612
10,888,378 B2 * 1/2021 Walch ................... A61F 2/4081
11,129,724 B2 * 9/2021 Knox .................... A61F 2/4014
11,628,067 B2 * 4/2023 Hodorek ............ A61B 17/1778 623/19.14
12,383,334 B2 * 8/2025 Chaoui .................. G06F 3/011
2012/0265315 A1 * 10/2012 Kusogullari .......... A61F 2/4003 623/19.14
2013/0018475 A1 * 1/2013 Vanasse ................ A61F 2/4003 623/19.14

(Continued)

OTHER PUBLICATIONS

"European Application Serial No. 24158964.7, Extended European Search Report mailed Jun. 17, 2024", 7 pgs.

(Continued)

*Primary Examiner* — Anu Ramana
(74) *Attorney, Agent, or Firm* — SCHWEGMAN LUNDBERG & WOESSNER, P.A.

(57) ABSTRACT

An orthopedic guide may include a cannulated shaft, a body and a plurality of arms. The body can be coupled to the cannulated shaft. The plurality of arms can extend radially outward from the body. One or more of the plurality of arms can include an outer radial end portion that has a length in a radial dimension configured to indicate a minimum safety boundary for a humeral implant relative to a cortex of a humerus.

20 Claims, 8 Drawing Sheets

(56) References Cited

U.S. PATENT DOCUMENTS

| | | | | |
|---|---|---|---|---|
| 2022/0296381 | A1 | 9/2022 | Ek et al. | |
| 2023/0148085 | A1 * | 5/2023 | Paul | A61B 34/10 606/87 |

OTHER PUBLICATIONS

"European Application Serial No. 24158964.7, Response filed Feb. 3, 2025 to Extended European Search Report mailed Jun. 17, 2024", 14 pgs.

* cited by examiner 300C
300E
300B
319
308
300D
300A
400

ORTHOPEDIC SHOULDER GUIDE

CLAIM OF PRIORITY

This application claims the benefit of U.S. Provisional Patent Application Ser. No. 63/447,372, filed on Feb. 22, 2023, the benefit of priority of which is claimed hereby, and which is incorporated by reference herein in its entirety.

FIELD OF THE DISCLOSURE

The present disclosure relates to an orthopedic shoulder guide that can be used during an arthroplasty procedure.

BACKGROUND

In the human body, tissue can require repair and replacement. Such tissue includes bone, muscles, tendons, ligaments and cartilage. For example, disease can necessitate replacement of bone(s) of the joint with one or more prosthetic components. Such replacement can require use of orthopedic guides and other instruments to facilitate proper orientation and/or size of the one or more prosthetic components.

The human shoulder joint may require repair or replacement. A conventional or reverse joint replacement may be used in a situation where the bone is diseased and/or a rotator cuff is damaged or lacking. This can provide pain relief and return the shoulder joint to normal kinematic function (e.g., the patient can again raise their arm above their head).

SUMMARY

The present disclosure provides orthopedic guides and systems that can be used in a shoulder arthroplasty. However, the concepts discussed herein can be extended to other guides and to other joints of the human body, and thus, can be applicable to orthopedic guides for the hip, knee, ankle, etc.

The present inventor has realized that determining a proper size and a desired placement for a humeral implant in a shoulder arthroplasty procedure can be complex and time consuming. The humeral implant can be available in a plurality of standard sizes. However, if the humeral implant that is selected is too large for the humerus, impingement and/or damage to the cortex of the humerus can occur. To avoid a poor outcome such as impingement and/or damage, surgeons typically image the humerus to ascertain if the size of the humerus is sufficient to accept the selected standard size of humeral implant in a depth dimension. However, imaging the humerus adds additional steps, cost and time to the procedure.

The present inventor has recognized a guide configured for determining the proper size and desired placement for the humeral implant. This guide can save time and can reduce surgical complexity in that it can eliminate the need for imaging. This can result in lower surgical costs among other benefits. In particular, the guide can be configured with a length and/or indicia in a radial dimension that captures/indicates a depth of the humeral implant. Put another way, the guide is equipped with a reference feature indicative of a depth of parts of the humeral implant that can potentially impinge/damage the cortex. Thus, the guide can be slightly larger in length in a radial dimension than a correspondingly sized humeral implant. This difference in the length in the radial dimension between the guide and the correspondingly sized humeral implant can indicate a minimum safety boundary for the humeral implant relative to a cortex of a humerus. For example, the guide is configured such that if an outer radial end portion of an arm of the guide contacts the cortex of the humerus, this indicates to the surgeon that a corresponding size of humeral implant is too large and a smaller size of humeral implant should be selected to avoid potential for impingement and/or damage to the cortex. This sizing process can be conducted easily and efficiently without the need for imaging the humerus.

Further benefits are recognized by the present inventor and can include that the humeral guide can have arms with a shape along a proximal surface that corresponds (other than the addition of the outer radial end portion on the arm that provides an indication of the minimum safety boundary) with a shape of arms of the humeral implant along a proximal surface. This can allow the surgeon to visualize implant placement and shape using the humeral guide prior to inserting a pin and implanting the humeral implant. This shape for the guide can aid the surgeon in determining a desired placement for the humeral implant.

The above discussion is intended to provide an overview of subject matter of the present patent application. It is not intended to provide an exclusive or exhaustive explanation of the invention. The description below is included to provide further information about the present patent application To better illustrate the apparatuses and systems disclosed herein, a non-limiting list of examples (discussed as aspects and techniques immediately below) is provided here:

In some aspects, the techniques described herein relate to an orthopedic guide for a shoulder arthroplasty optionally including: a cannulated shaft; a body coupled to the cannulated shaft; and a plurality of arms extending radially outward from the body, wherein one or more of the plurality of arms include an outer radial end portion that has a length in a radial dimension configured to indicate a minimum safety boundary for a humeral implant relative to a cortex of a humerus.

In some aspects, the techniques described herein relate to an orthopedic guide, wherein optionally each of the plurality of arms includes one or more fins projecting tangentially outward therefrom, and wherein the one or more fins are positioned radially inward of the outer radial end portion.

In some aspects, the techniques described herein relate to an orthopedic guide, wherein optionally the one or more fins have a width in a tangential direction that corresponds to a width in the tangential direction of one or more fins of the humeral implant.

In some aspects, the techniques described herein relate to an orthopedic guide, wherein optionally the one or more fins of the humeral implant form an outermost edge of the humeral implant.

In some aspects, the techniques described herein relate to an orthopedic guide, wherein optionally the length of the outer radial end portion is based upon both a depth of the one or more fins of the humeral implant and a radial position of the one or more fins of the humeral implant from a centerline axis of the humeral implant.

In some aspects, the techniques described herein relate to an orthopedic guide, wherein, optionally except for the outer radial end portion, a shape of the plurality of arm as measured along a proximal surface thereof corresponds to a shape of a plurality of arms of the humeral implant as measured along a proximal surface thereof.

In some aspects, the techniques described herein relate to an orthopedic guide, wherein optionally the length of the outer radial end portion is based upon both a maximum depth of the humeral implant and a maximum diameter of the humeral implant.

In some aspects, the techniques described herein relate to an orthopedic guide, wherein optionally together the cannulated shaft and body form an aperture configured to guide a pin into the humerus.

In some aspects, the techniques described herein relate to an orthopedic guide, further optionally including indicia on one of the plurality of arms configured to be aligned with a superior lateral line of the humerus.

In some aspects, the techniques described herein relate to an orthopedic guide, wherein optionally each of the plurality of arms has the outer radial end portion, and wherein the length of the outer radial end portion for each of the plurality of arms differs.

In some aspects, the techniques described herein relate to an orthopedic guide, wherein optionally the length of the outer radial end portion is determined based upon an anatomical modeling system that analyzes a population of humerus bones from a plurality of patients.

In some aspects, the techniques described herein relate to an orthopedic system for a shoulder arthroplasty optionally including: a humeral implant configured for fixation to a humerus, wherein the humeral implant has a proximal surface with a first distance as measured in a radial dimension from a centerline axis of the humeral implant; and a guide configured to place the humeral implant at a respected proximal surface of the humerus, wherein the guide has a proximal surface with a second distance as measured in a radial dimension from a centerline axis of the guide that differs from the first distance by a length in the radial dimension configured to indicate a minimum safety boundary for the humeral implant relative to a cortex of a humerus.

In some aspects, the techniques described herein relate to an orthopedic system, wherein optionally the length is determined based upon an anatomical modeling system that analyzes a population of humerus bones from thousands of patients.

In some aspects, the techniques described herein relate to an orthopedic system, wherein optionally the length is based upon both a depth and the first distance of the proximal surface of the humeral implant.

In some aspects, the techniques described herein relate to an orthopedic system, wherein optionally the proximal surface of the guide has a configuration corresponding to the proximal surface of the humeral implant save for the length in the radial dimension.

In some aspects, the techniques described herein relate to an orthopedic system, wherein optionally: the humeral implant includes a body and a plurality of arms that form the proximal surface of the humeral implant, wherein the plurality of arms have one or more fins at an outer radial end configured for fixation to the humerus; and the guide having a body and a plurality of arms that form the proximal surface of the guide, wherein the plurality of arms have one or more fins corresponding in size and position to the one or more fins of the humeral implant, wherein the plurality of arms of the guide each have of an outer radial end portion that extends radially outward from the one or more fins of the guide, and wherein a length of the outer radial end portion in the radial dimension corresponds to the length in the radial dimension configured to indicate the minimum safety boundary.

In some aspects, the techniques described herein relate to an orthopedic system, wherein optionally; the humeral implant includes a plurality of humeral implants each having a different standard size; and the guide includes a plurality of guides each having a different size, wherein the different size corresponds with the different standard size of the humeral implants save for the outer radial end portion on each of the plurality of arms of the plurality of guides.

In some aspects, the techniques described herein relate to an orthopedic system, wherein optionally the length of the outer radial end portion for each of the plurality of arms differs and includes a unique length in the radial dimension.

In some aspects, the techniques described herein relate to an orthopedic guide for a shoulder arthroplasty optionally including: a cannulated shaft; a body coupled to the cannulated shaft; and a plurality of arms extending radially outward from the body, wherein each of the plurality of arms has an outer radial end portion configured to indicate a minimum safety boundary for a humeral implant relative to a cortex of a humerus, wherein each outer radial end portion has a different length in a radial dimension based at least in part on a shape of the cortex including a depth of the cortex.

In some aspects, the techniques described herein relate to an orthopedic guide, wherein optionally the different length in the radial dimension of each outer radial end portion is determined based upon an anatomical modeling system that analyzes a population of humerus bones from a plurality of patients.

In some aspects, the techniques described herein relate to an orthopedic guide, wherein optionally each of the plurality of arms includes one or more fins projecting tangentially outward therefrom, and wherein the one or more fins are positioned radially inward of the outer radial end portion.

In some aspects, the techniques described herein relate to an orthopedic guide, wherein optionally the one or more fins have a width in a tangential direction that corresponds to a width in the tangential direction of one or more fins of the humeral implant.

In some aspects, the techniques described herein relate to an orthopedic guide, wherein optionally the one or more fins of the humeral implant form an outermost edge of the humeral implant.

In some aspects, the techniques described herein relate to an orthopedic guide, wherein optionally the different length in the radial dimension of each outer radial end portion is based at least in part on both a depth of the one or more fins of the humeral implant and a radial position of the one or more fins of the humeral implant from a centerline axis of the humeral implant.

In some aspects, the techniques described herein relate to an orthopedic guide, wherein, optionally except for the outer radial end portion, a shape of the plurality of arm as measured along a proximal surface thereof corresponds to a shape of a plurality of arms of the humeral implant as measured along a proximal surface thereof.

In some aspects, the techniques described herein relate to an orthopedic guide, wherein optionally the different length in the radial dimension of each outer radial end portion is based at least in part on both a maximum depth of the humeral implant and a diameter of the humeral implant.

In some aspects, the techniques described can include any one or combination of the apparatus and system examples above including any one or combination of the individual features disclosed herein.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the disclosure is not intended to be limited to any specific terms or illustrations used herein, and it is to be understood that each specific term includes all technical equivalents.

The present disclosure is directed to apparatuses and systems that can be used in joint replacement procedures such as a shoulder arthroplasty. The joint replacement procedures can be total or partial procedures such as an anatomic shoulder arthroplasty. Although the present methods, apparatuses and systems are being described in reference to a shoulder arthroplasty, the apparatuses and systems can be used for other joints where orthopedic guides are utilized.

Figure 1:
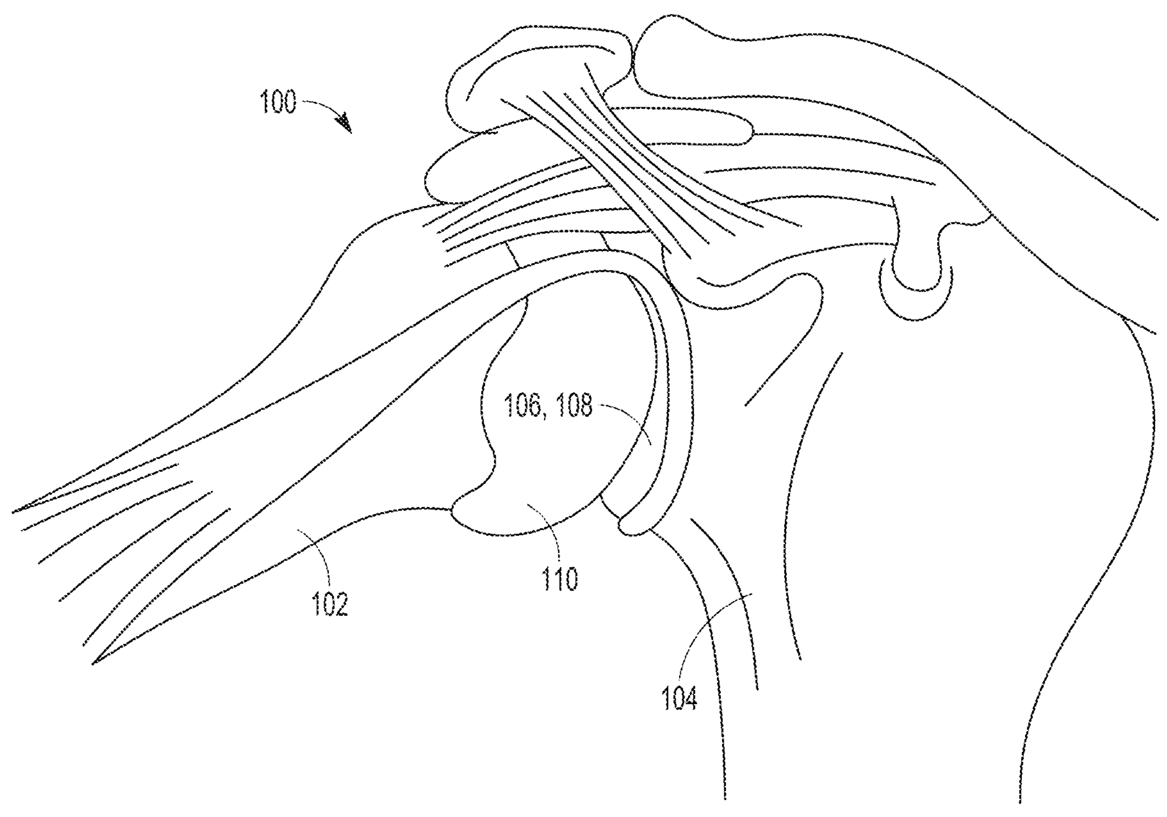
FIG. 1 is an anatomic view of a shoulder joint of a patient.

FIG. 1 illustrates a shoulder joint 100 with several ligaments stripped away. As shown, the shoulder joint 100 includes a humerus 102 and a scapula 104 that has a glenoid 106 with a socket 108 for interacting with a humeral head 110 of humerus 102. Humeral head 110 can articulate within socket 108 to allow for normal motion of the shoulder joint 100. Disease can degenerate the bone or soft tissue of the humeral head 110 and/or scapula 104. These can cause pain and/or can negatively impact shoulder joint function. Typically, a surgical intervention may be required to replace the shoulder joint and restore shoulder joint function.

Figure 2:
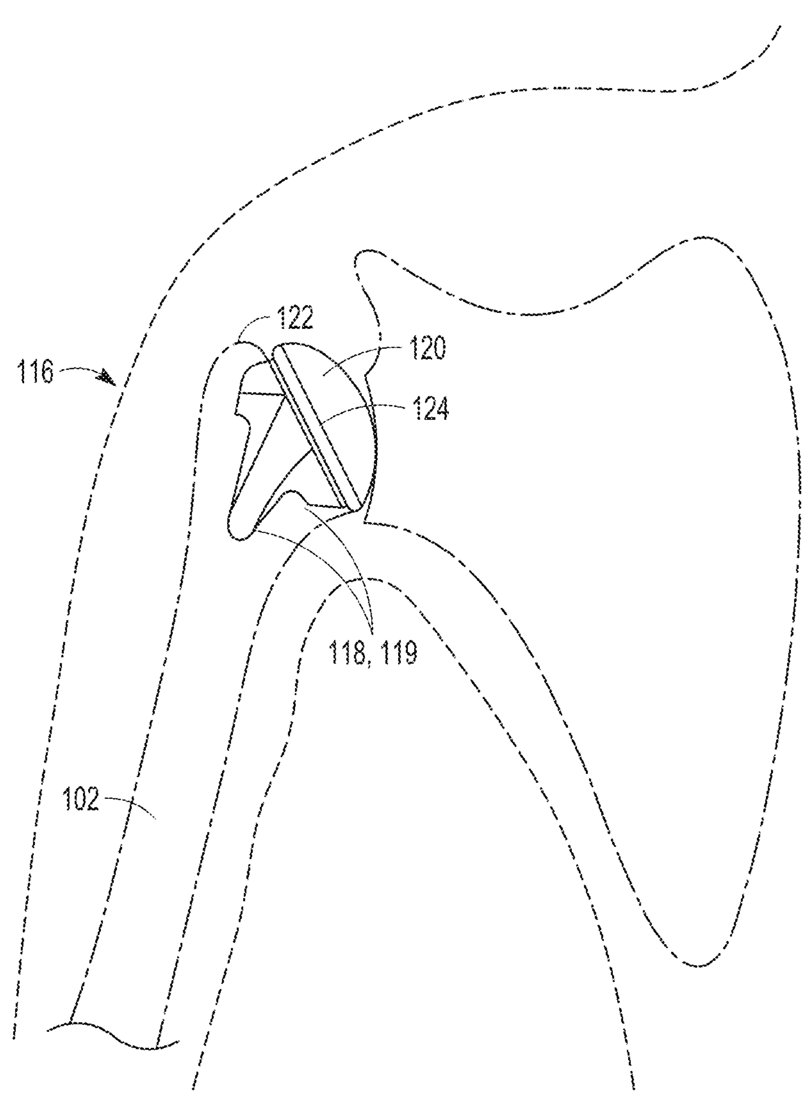
FIG. 2 is a schematic diagram of a prosthesis assembly implanted in a humerus of the patient and forming at least a portion of the shoulder joint.

FIG. 2 illustrates a schematic diagram of a prosthesis assembly 116 installed at the shoulder joint 100. The prosthesis assembly 116 can include a humeral implant 118 (also called a humeral implant component, humeral component, humeral implant or humeral prosthesis herein) and a head component 120.

The humeral implant 118 can be fitted into a recess 119 formed at a proximal end portion 122 of the humerus 102. The embodiment of FIG. 2 (and indeed the embodiments of FIGS. 3, 4 and 6B) show a stem-less or stem-free design for the prosthesis assembly 116. Thus, the humeral implant 118 does not couple with a stem, which would be typical in a total shoulder replacement procedure. The humeral implant 118 without the stem can be used in a partial shoulder replacement procedure. It is contemplated that the systems and methods disclosed herein could be used with any applicable joint replacement procedure including a total shoulder replacement procedure. Thus, the concepts of the present application are not limited by the stem-less or stem-free design examples provided herein. Similarly, the example bone of the humerus should not be interpreted as limiting but merely exemplary.

As shown in FIG. 2, a proximal side 124 of the humeral implant 118 can interface with the head component 120. The head component 120 can couple with the humeral implant 118 using known mechanisms such as mating taper features and intermediate component or the like. The head component 120 can be semi-spherical or otherwise shaped to replicate the head of the humerus (which is removed during the joint replacement procedure).

Figure 3:
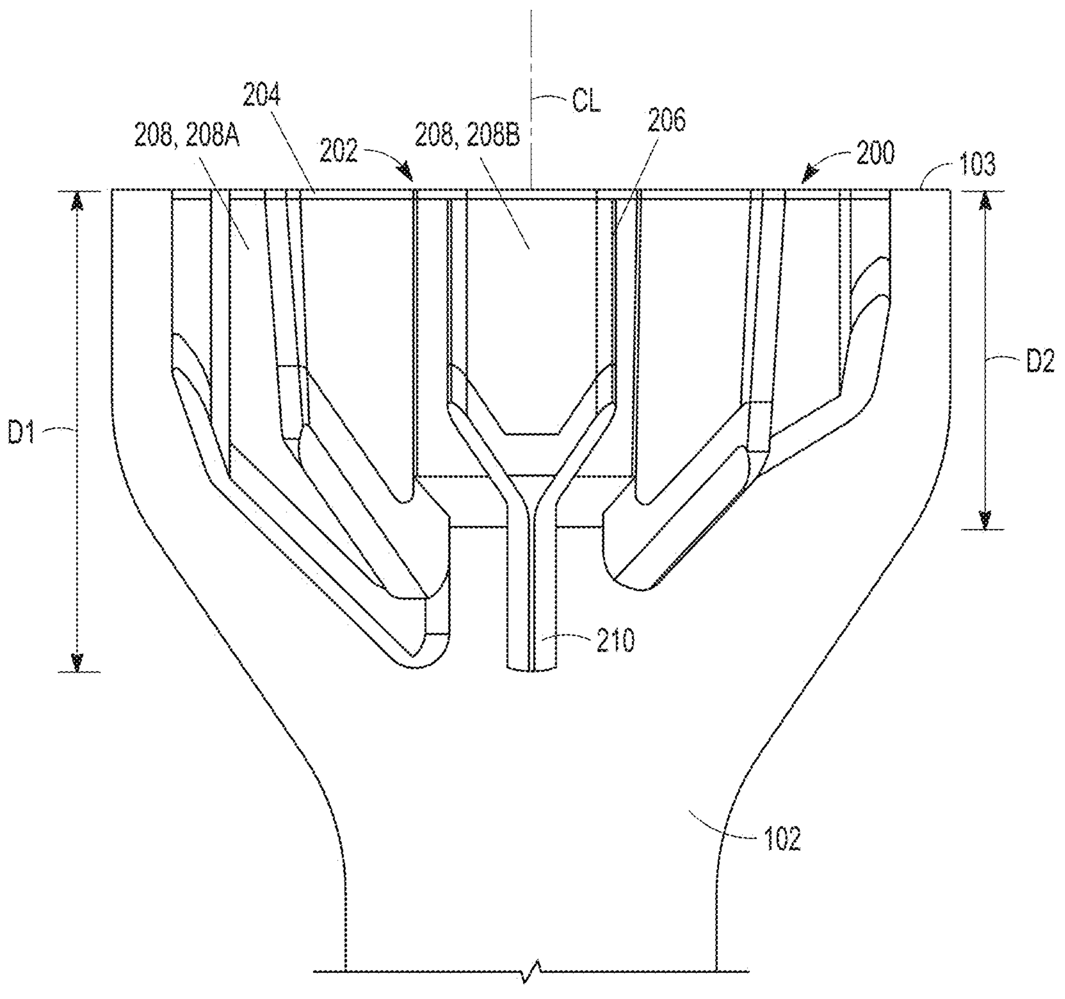
FIG. 3 is a plan view of an first side of a humeral implant of the prosthesis assembly implanted in the humerus according to an example of the present application.
Figure 4:
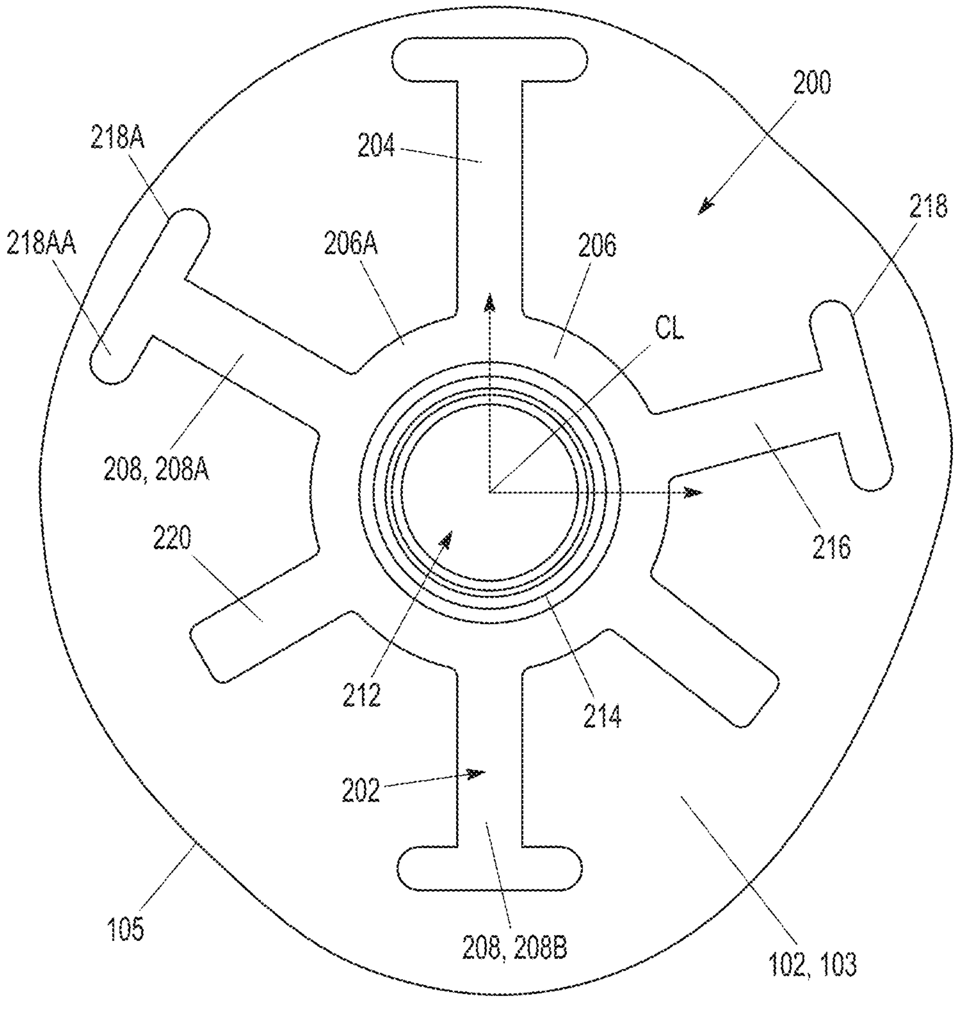
FIG. 4 is a plan view of a proximal side of the humeral implant of FIG. 3 implanted in a resected portion of the humerus according to an example of the present application.

FIGS. 3 and 4 show an example of a humeral implant 200 implanted in the humerus 102 at a resected surface 103. The humeral implant 200 can be configured in the manner of the Sidus® Stem-Free Shoulder prosthesis, Comprehensive® Nano Stemless Shoulder or another commercially available and manufactured by Zimmer Biomet Inc., of Warsaw Indiana. The humeral implant designs shown in FIGS. 3, 4 and 6B are purely exemplary and are provided merely to facilitate practitioner understanding.

As shown in FIGS. 3 and 4, the humeral implant 200 includes a proximal side 202 having a proximal surface 204, a body 206 and arms 208. FIG. 3 illustrates the humeral implant 200 inserted down into the humerus 102 guided by a pin 210 received by an aperture in the body 206. The pin 210 positions the humeral implant 200 with a desired position (e.g., at a center of a resected surface 103) relative to the humerus 102. The pin 210 can be arranged extending along a centerline axis CL of the humeral implant 200.

FIG. 4 shows the body 206 and the arms 208 from the proximal side 202 in greater detail. The body 206 can define an aperture 212 and a coupling feature 214. The aperture 212 can align with and the body 206 can define the centerline axis CL of the humeral implant 200. The arms 208 can each include an inner radial portion 216 and fins 218. As shown in FIG. 4, the humeral implant 200 can additionally include projections 220.

As shown in FIG. 4, the aperture 212 can extend through the body 206 from the proximal side 202 to a distal side. The aperture 212 can be sized to receive the pin 210 (FIG. 3). The pin 210 can set a location for the humeral implant 200 relative to the humerus 102. The coupling feature 214 can comprise a taper, thread or other mechanical feature configured to attach with a corresponding feature of the head component (e.g., the head component 120 of FIG. 2) or an intermediate component to the head component. The body 206 can have a cylindrical or ring shape that provides a hub for the arms 208 and the projections 220.

FIG. 4 shows the humeral implant 200 positioned in a central of the resected surface 103 of the humerus 102. FIG. 4 shows a cortex 105 of the humerus 102 and the humeral implant 200 positioned adjacent but within the cortex 105. The cortex 105 additionally extends in a depth dimension into the page distal of the humeral implant 200. The cortex 105 can vary in size and shape in the depth dimension from the size and shape shown in FIG. 4.

The term "proximal" refers to the general orientation of the side and/or surface when the humeral implant or humeral guide is implanted in the bone. Thus, "proximal" refers to a direction or location generally in the direction of or toward the head of a patient, and "distal" refers to the opposite direction of proximal, i.e., away from the head of a patient. As used herein, the terms "anterior" and "posterior" should be given their generally understood anatomical interpretation. Thus, "posterior" refers to a location or direction generally toward a rear of the patient. Similarly, "anterior" refers to a location or direction generally toward a front of the patient. Thus, "posterior" refers to the opposite direction of "anterior." Similarly, the terms "medial" and "lateral" should be given their generally understood anatomical interpretation. "Medial" refers to the more inward facing (inner part) of the prosthesis or guide (when in the implanted orientation) and "lateral" refers to the outer part or outward facing part. "Medial" refers to the opposite direction of "lateral."

Referring again to FIG. 3, when implanted in the humerus 102 the proximal side 202 of the humeral implant 200 can be located at or adjacent a proximal edge of the humerus 102 that is formed by the resected surface 103. The body 206 and the arms 208 can have various depths in a distal direction away from the proximal surface 204. Thus, for example, the arm 208A can have a greater depth D1 than a depth D2 of arm 208B. Indeed, the arm 208B can have a maximum depth that is less than the depth D1 of the arm 208A. The fins 218 can extend distally with the arms 208 from the proximal surface 204. The fins 218 can be configured to aid in anchoring the humeral implant 200 in the humerus 102. Additionally, the arms 208 can each have a different length and orientation relative to the centerline axis CL. The different depth of the arms 208 can position them at different relative locations adjacent the cortex 105 (FIG. 4).

The arms 208 can connect with the body 206. The arms 208 can be integral with or can be coupled to the body 206. FIG. 4 shows the arms 208 and the projections 220 extending outward from the body 206. The arms 208 extend outward in a radial dimension relative to the centerline axis CL of the humeral implant 200. The fins 218 can form an outer radial end of each of the arms 208. Thus, the fins 218 can connect with and can be positioned radially outward of the inner radial portion 216. Each arm 208 can include two fins (e.g., 218A and 218AA for the arm 208A). The fin 218A can be on an opposing side of the arm 208A from the fin 218AA. The fins 218 can project tangentially outward from the outer radial end of each arm 208. However, a single fin or three or more fins per arm is also contemplated.

A length of the arms 208 in the radial dimension and the depth of each of the respective arms 208 can be based upon an average anatomy derived from three- or two-dimensional scans of the relevant bone (here the humerus) using X-Ray, MRI, CT, ultrasound or other imaging techniques. Such shaping can include use of large number of scans and the ZiBRA™ or other Anatomical Modeling System to analyze thousands of bones, both male and female, representing a diverse global population.

Collectively, the body 206 and the arms 208 including the inner radial portion 216 and the fins 218 can form at least part of the proximal surface 204. Each of the arms 208 can have a different length in the radial dimension from the centerline axis CL. Thus, the arm 208A can have a length that is greater than the arm 208B, for example. This difference in length can be due to the different anatomical shape of the humerus 102 in the various directions (e.g., medial, lateral, depth (proximal-distal), anterior and posterior).

Figure 5:
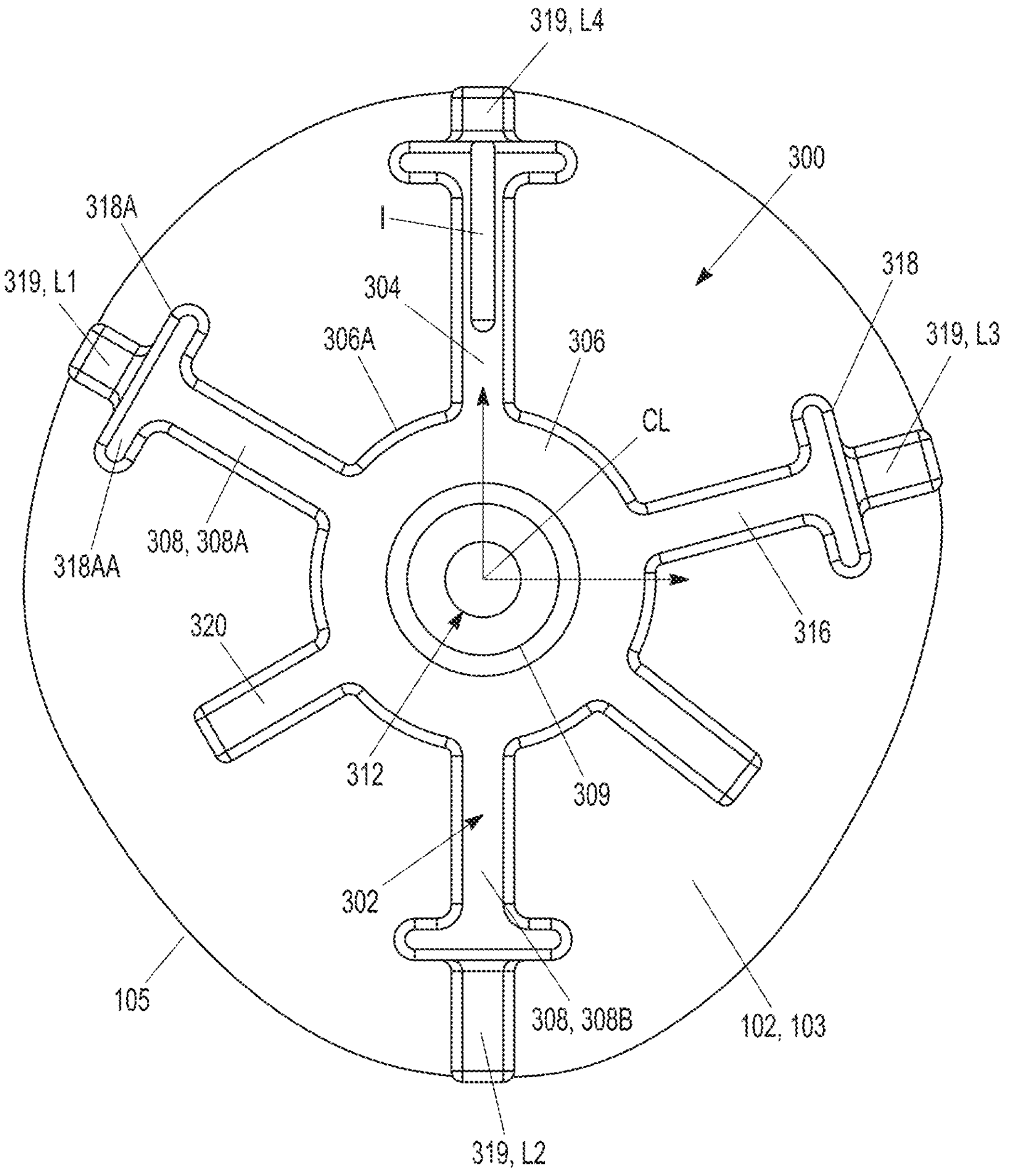
FIG. 5 is a plan view of a proximal side of a humeral guide of a corresponding size to the humeral implant of FIGS. 3 and 4 positioned adjacent the resected portion of the humerus according to an example of the present application.
Figure 6A:
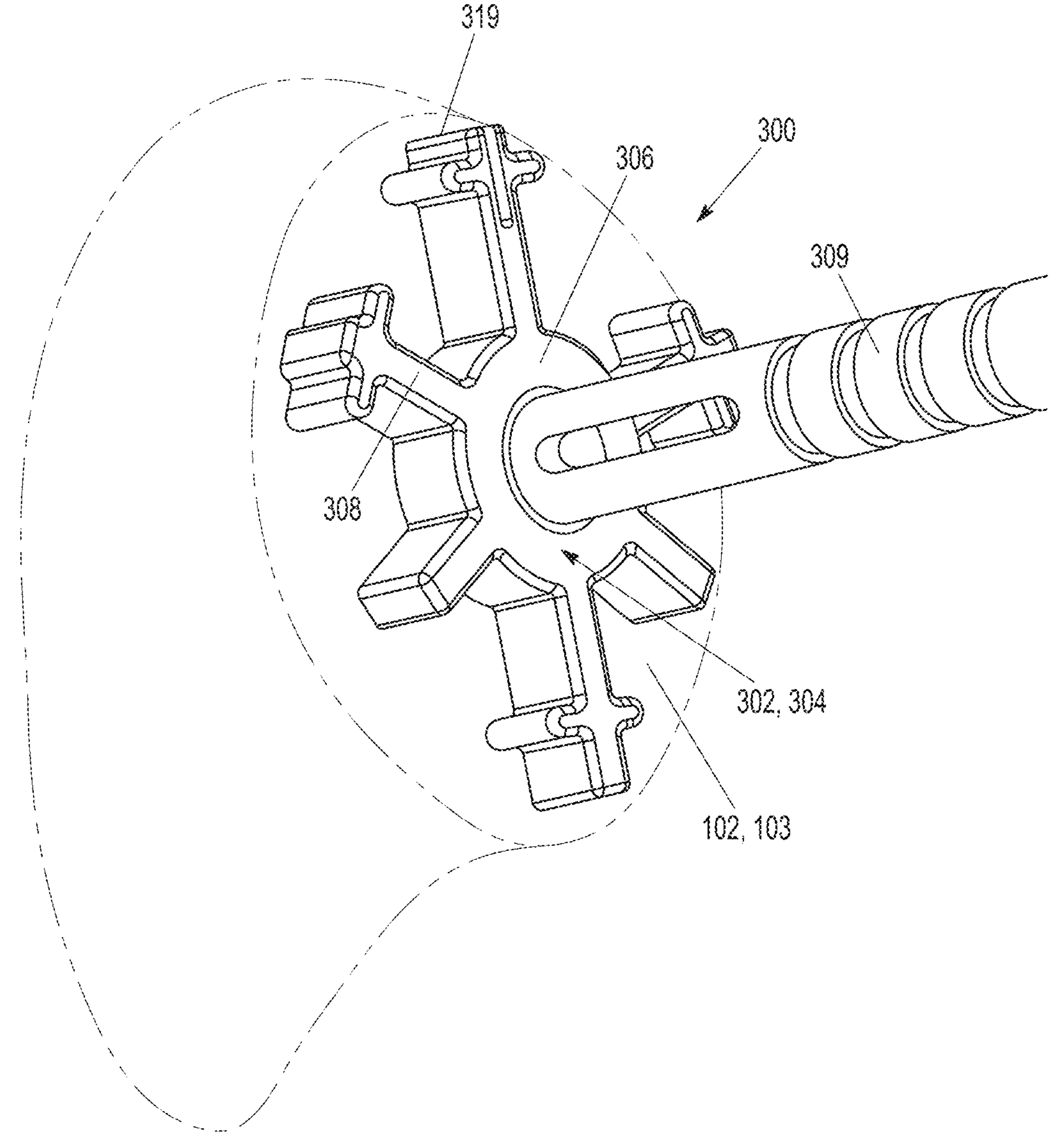
FIG. 6A is a perspective view of the humeral guide of FIG. 5 positioned adjacent the humerus according to an example of the present application.
Figure 6B:
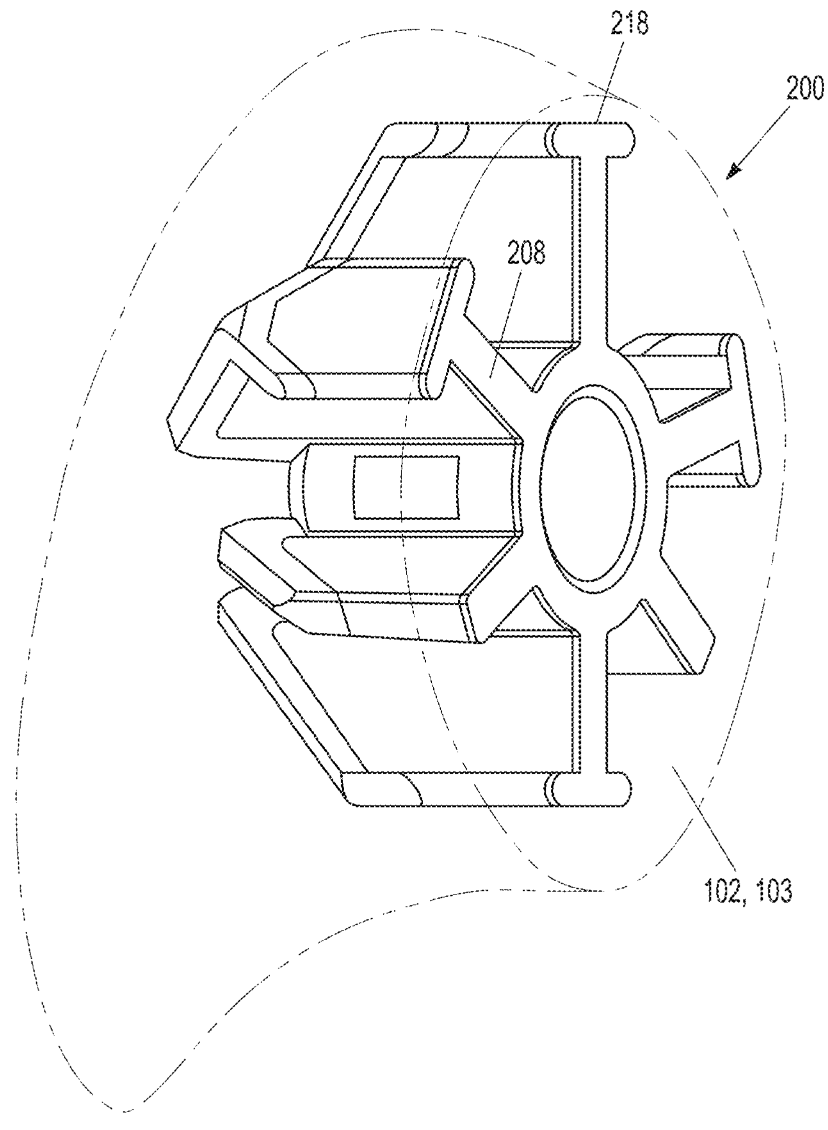
FIG. 6B is a perspective view of the humeral implant of FIG. 3 implanted in the humerus according to an example of the present application

FIGS. 5 and 6A show a humeral guide 300 positioned adjacent the humerus 102 and adjacent the resected surface 103. FIG. 5 illustrates the humeral guide 300 positioned relative to the cortex 105 of the humerus 102. The humeral guide 300 includes a proximal side 302 having a proximal surface 304, a body 306 and arms 308. As best shown in FIG. 6A, the humeral guide 300 can additionally include a cannulated shaft 309 or tube that is coupled to and extends proximal of the body 306. Together the body 306 and the cannulated shaft 309 can define an aperture 312 (FIG. 5) configured to receive and guide the pin 210 (FIG. 3) into the humerus 102. The humeral guide 300 can be configured to position the pin 210 (e.g., at a center of the resected surface 103) relative to the humerus 102. Additionally, the humeral guide 300 can be configured to determine an appropriate size for the humeral implant (e.g., the humeral implant 200).

FIG. 5 shows an example were a size large "L" humeral guide 300 corresponding to a size large "L" humeral implant is positioned relative to the humerus 102 including the cortex 105. Several arms 308 including arm 308A and arm 308B of the humeral guide 300 when positioned relative to the resected surface 103 of the humerus 102 overlap with the cortex 105. This indicates to the surgeon that the size large humeral implant may impinge on the cortex 105 in the depth dimension with possible negative results if implanted. Thus, the humeral guide 300 can be swapped by the surgeon for a more appropriately sized "medium" humeral guide and a corresponding size medium humeral implant.

As shown in FIGS. 4 and 5, with one or more exceptions noted below, the shape and/or size of the humeral guide 300 along the proximal surface 304 of the arms 308 can generally correspond with the shape and/or size of the humeral implant 200 along the proximal surface 204 of the arms 208. Thus, for example, the fins 218 can have a same shape, a same relative position and/or a same size as the fins 318. This allows the surgeon to visualize placement and configuration of the humeral implant 200 with the humeral guide 300. Difference(s) between the shape and/or size of the humeral guide 300 along the proximal surface 304 or the arms 308 and the proximal surface 204 of the arms 208 of the humeral implant 200 are discussed below in further detail.

FIG. 5 shows the body 306 and the arms 308 from the proximal side 302. The body 306 can define part of the aperture 312 and can be coupled to the cannulated shaft 309. An exterior side surface 306A of the body 306 can have substantially a same shape and/or size as an exterior side surface 206A of the body 206 of the humeral implant 200 (FIG. 4), for example. The aperture 312 defined by the body 306 and the cannulated shaft 309 can define the centerline axis CL of the humeral guide 300. The centerline axis CL can be coaxial with a center of the aperture 312, the body 306 and the cannulated shaft 309. The arms 308 can each include an inner radial portion 316, fins 318 and an outer radial end portion 319. As shown in FIG. 4, the humeral guide 300 can additionally include projections 320.

The arms 308 can connect with the body 306. The arms 308 can be integral with or can be coupled to the body 306. FIG. 5 shows the arms 308 and the projections 320 extending outward from the body 306. The arms 308 extend outward in a radial dimension relative to the centerline axis CL of the humeral guide 300. Collectively the body 306 and the arms 308 including the inner radial portion 316, the fins 318 and the outer radial end portion 319 can form the proximal surface 304. Each of the arms 308 can include a different length in the radial dimension from the centerline axis CL.

The fins 318 can connect with and can be positioned radially outward of the inner radial portion 316 but can be located inward radially from the outer radial end portion 319. Each arm 308 can include two fins (e.g., 318A and 318AA for the arm 308A). The fin 318A can be on an opposing side of the arm 308A from the fin 318AA. The fins 318 can project tangentially outward from each arm 308. One or more of the arms 308 can include indicia I configured to be aligned with a superior lateral line or another anatomic feature of the humerus 102.

The arms 308 can be configured to correspond to the arms 208 (FIG. 4) in one or more of a size and/or shape with the exception of the addition of the outer radial end portion 319 and/or in a depth. Additionally, the arms 308 can be positioned in a same relative position with regard to the body 306 as the arms 208 are relative to the body 206. Thus, the fins 318 can have one or more of substantially a same size, a same shape and/or a same position as the fins 218 (FIG. 4) with the same pin location utilized. Similarly, the inner radial portion 316 can have one or more of substantially a same size, a same shape and/or same position as the inner radial portion 216 (FIG. 4). The outer radial end portion 319 can extend radially outward from the fins 318. Thus, the fins 318 are positioned radially inward of the outer radial end portion 319. This arrangement for the fins 318 differs from that of the fins 218 (FIG. 4) where the fins 218 form or are positioned at the outermost radial end of the arms 208.

The outer radial end portions 319 can each have a length (L1, L2, L3 and L4) in a radial dimension configured to indicate a minimum safety boundary for the humeral implant (e.g., the humeral implant 200) relative to the cortex 105 of the humerus 102. As discussed above and shown in FIG. 5, due to the size of the humeral implant 200 and the humeral guide 300 being too large, the minimum safety boundary for the humeral guide 300 relative to the cortex 105 is not satisfied. This is because one or more of the outer radial end portions 319 overlap with the cortex 105 as discussed previously. The length (L1, L2, L3 and L4) of each of the outer radial end portions 319 is dependent upon several factors. These factors can include, but are not limited to, any one or combination of: a maximum depth of the humeral implant 200, a depth of a respective corresponding arm 208 (FIG. 4) of the humeral implant 200, a maximum diameter of the humeral implant 200, a size and shape of the humerus 102 including in a depth dimension and/or a length of a respective corresponding arm 208 (FIG. 4) in the radial dimension. The length (L1, L2, L3 and L4) of each of the outer radial end portions 319 can also be dependent upon a different factor of safety then is applied to the arms 208, which recall, had a length and a depth based upon an average anatomy derived from ZiBRA™ or other Anatomical Modeling System.

Each of the outer radial end portions 319 can have a unique/different length (L1, L2, L3 and L4) in the radial dimension. Thus, the length of each of the arms 308 in the radial dimension can differ. As an example, the length L1 of the outer radial end portion 319 of the arm 308A (corresponding to the arm 208A of FIG. 4) can be less than a length L2 of the outer radial end portion 319 of the arm 308B (corresponding to the arm 208B of FIG. 4). This difference in the length L2 v. L1 can be a result of the shape of the cortex 105, a depth of the cortex 105, a length of the arm 208A v. the length of the arm 208B and/or a depth of the arm 208A v. a depth of the arm 208B. As noted above in regard to FIG. 3, the depth D1 of the arm 208A can be greater than the depth D2 of arm 208B (see FIG. 3). This difference in the depths D1 and D2 can impact the distance each arm 208A and 208B should be located from the cortex 105. The length (L1, L2, L3 and L4) of the outer radial end portions 319 in the radial dimension can differ because of different depths of the arms 208. Thus, the length (L1, L2, L3 and L4) of the outer radial end portions 319 can depend upon the depth and/or other geometry of the humeral implant 200 and/or the geometry of the humerus 102. The length (L1, L2, L3 and L4) of the outer radial end portions 319 can depend upon a depth of respective of the fins 218 of the humeral implant 200 and a radial position of respective of the fins 218.

FIG. 6B shows the humeral implant 200 positioned in a similar relative position as the humeral guide 300 of FIG. 6A but implanted in the resected surface 103 of the humerus 102. Save for the outer radial end portions 319, the humeral guide 300 along the proximal surface 304 of the arms 308 can have a corresponding size and/or shape as the proximal surface 204 of the arms 208 of the humeral implant 200. Additionally, the maximum depth of the humeral implant 200 and/or the depth of the arms 208 (including at the fins 218) can differ from a depth of those corresponding features of the humeral guide 300. The depth of the humeral guide 300 can be substantially the same along the arms 308, providing the humeral guide 300 with a substantially uniform thickness.

Figure 7:
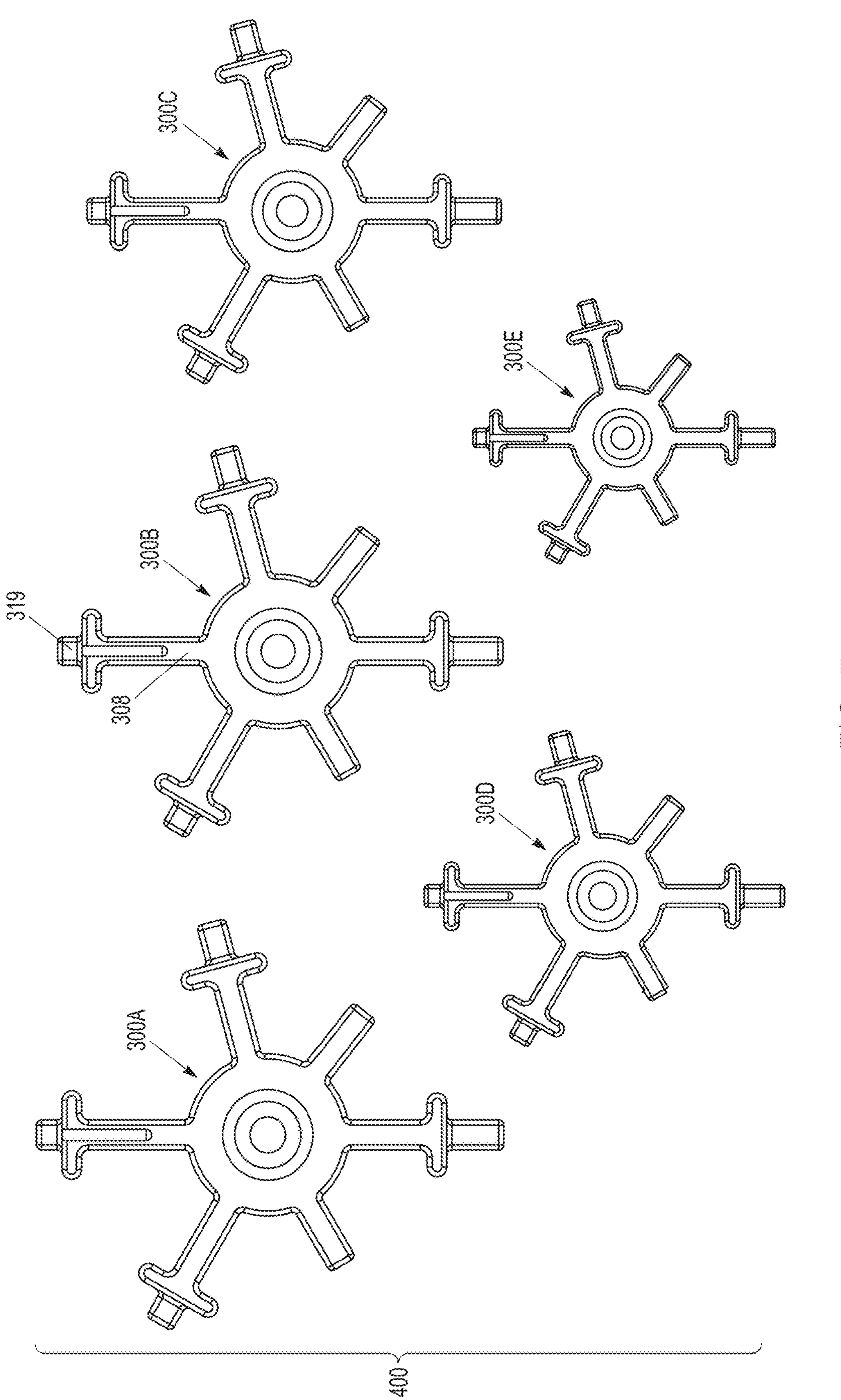
FIG. 7 is a plan view of a system of different sized humeral guides according to an example of the present application.

FIG. 7 shows a system 400 of humeral guides 300A, 300B, 300C, 300D and 300E each having a different size from one another. Each humeral guide 300A, 300B, 300C, 300D and 300E can correspond with a standard size of the humeral implant 200 (FIGS. 3, 4 and 6B). Thus, the humeral guide 300 (and the humeral implant 200) can include five distinct sizes (such as x-small, small, medium, large and x-large). The outer radial end portions 319 of each of the humeral guides 300A, 300B, 300C, 300D and 300E can differ in length in the radial dimension. Thus, the outer radial end portions 319 for each of the humeral guides 300A, 300B, 300C, 300D and 300E can each have a unique/different length from one another in the radial dimension. Furthermore, the length of the outer radial end portions 319 may not simply just be a linearly scaled down length from one size to the next smaller size but can change from one size to the next smaller size in a non-linear manner. Thus, each of the arms 308 for all of the humeral guides 300A, 300B, 300C, 300D and 300E can be specifically configured to a have a desired length in the radial dimension.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An orthopedic guide for a shoulder arthroplasty comprising:

a cannulated shaft;

a body coupled to the cannulated shaft; and a plurality of arms extending radially outward from the body, wherein one or more of the plurality of arms include an outer radial end portion that has a length in a radial direction relative to a centerline axis of the cannulated shaft, the length of the outer radial end portion configured to indicate a minimum safety boundary for a humeral implant relative to a cortex of a humerus.

2. The orthopedic guide of claim 1, wherein each of the plurality of arms includes one or more fins projecting tangentially outward from each of the plurality of arms, and wherein the one or more fins are positioned radially inward of the outer radial end portion.

3. The orthopedic guide of claim 2, wherein the one or more fins have a width in a tangential direction that corresponds to a width in the tangential direction of one or more fins of the humeral implant.

4. The orthopedic guide of claim 3, wherein the one or more fins of the humeral implant form an outermost edge of the humeral implant.

5. The orthopedic guide of claim 4, wherein the length of the outer radial end portion is based upon both a depth of the one or more fins of the humeral implant and a radial position of the one or more fins of the humeral implant from a centerline axis of the humeral implant.

6. The orthopedic guide of claim 1, wherein, except for the outer radial end portion, a shape of a boundary encompassing the plurality of arms collectively as measured along a proximal surface thereof corresponds to a shape of a boundary encompassing a plurality of arms collectively of the humeral implant as measured along a proximal surface thereof.

7. The orthopedic guide of claim 6, wherein the length of the outer radial end portion is based upon both a maximum depth of the humeral implant and a maximum diameter of the humeral implant.

8. The orthopedic guide of claim 1, wherein together the cannulated shaft and body form an aperture configured to guide a pin into the humerus.

9. The orthopedic guide of claim 1, further comprising indicia on one of the plurality of arms configured to be aligned with a superior lateral line of the humerus.

10. The orthopedic guide of claim 1, wherein each of the plurality of arms has the outer radial end portion, and wherein the length of the outer radial end portion for each of the plurality of arms differs.

11. The orthopedic guide of claim 1, wherein the length of the outer radial end portion is determined based upon an anatomical modeling system that analyzes a population of humerus bones from a plurality of patients.

12. An orthopedic system for a shoulder arthroplasty comprising:

a humeral implant configured for fixation to a humerus, wherein the humeral implant has a body, a centerline axis, and a plurality of arms extending radially outward from the body, each of the plurality of arms has an outermost radial end at a first distance measured in a radial direction from a centerline axis of the humeral implant; and a guide configured to place the humeral implant at a respective proximal surface of the humerus, wherein the guide has a body, a centerline axis, and a plurality of arms extending radially outward from the body of the guide, wherein each of the plurality of arms of the guide has an outer radial end portion that extends radially outward from an outermost surface of a corresponding one of the plurality of arms of the guide and wherein a length of the outer radial end portion in a radial direction indicates a minimum safety boundary for the humeral implant relative to a cortex of a humerus.

13. The orthopedic system of claim 12, wherein the length is determined based upon an anatomical modeling system that analyzes a population of humerus bones from thousands of patients.

14. The orthopedic system of claim 12, wherein the length is based upon both a depth and the first distance of a proximal surface of the humeral implant.

15. The orthopedic system of claim 12, wherein a proximal surface of the guide has a configuration corresponding to the proximal surface of the humeral implant except for the length of the outer radial end portion in the radial direction.

16. The orthopedic system of claim 12, wherein:

the humeral implant includes a body and a plurality of arms that form a proximal surface of the humeral implant, wherein each of the plurality of arms has a fin at an outer radial end configured for fixation to the humerus; and the guide having a body and a plurality of arms that form the proximal surface of the guide, wherein each of the plurality of arms has a fin corresponding in size and position to the fin of the humeral implant, wherein each of the plurality of arms of the guide has an outer radial end portion that extends radially outward from an outer surface of the fin of the guide, and wherein a length of the outer radial end portion in the radial direction indicates the minimum safety boundary.

17. The orthopedic system of claim 16, wherein;

the humeral implant comprises a plurality of humeral implants each having a different standard size; and the guide comprises a plurality of guides each having a different size, wherein each different size guide corresponds to each different size humeral implant excluding the outer radial end portion on each of the plurality of arms of the guide.

18. The orthopedic system of claim 17, wherein the length of the outer radial end portion for each of the plurality of arms differs and comprises a unique length in the radial direction.

19. An orthopedic guide for a shoulder arthroplasty comprising:

a cannulated shaft;

a body coupled to the cannulated shaft; and a plurality of arms extending radially outward from the body, wherein each of the plurality of arms has an outer radial end portion configured to indicate a minimum safety boundary for a humeral implant relative to a cortex of a humerus, wherein each outer radial end portion has a different length in a radial direction relative to a centerline axis of the cannulated shaft, the different length of each outer radial end portion based at least in part on a shape of the cortex including a depth of the cortex.

20. The orthopedic guide of claim 19, wherein the different length in the radial direction of each outer radial end portion is determined based upon an anatomical modeling system that analyzes a population of humerus bones from a plurality of patients, wherein each of the plurality of arms includes one or more fins projecting tangentially outward therefrom, wherein the one or more fins are positioned radially inward of the outer radial end portion, and wherein the one or more fins have a width in a tangential direction that corresponds to a width in the tangential direction of one or more fins of the humeral implant.

* * * * *